United States Patent [19]

Fong

[11] Patent Number: 4,479,911
[45] Date of Patent: * Oct. 30, 1984

[54] PROCESS FOR PREPARATION OF MICROSPHERES AND MODIFICATION OF RELEASE RATE OF CORE MATERIAL

[75] Inventor: Jones W. Fong, Parsippany, N.J.

[73] Assignee: Sandoz, Inc., E. Hanover, N.J.

[*] Notice: The portion of the term of this patent subsequent to May 24, 2000 has been disclaimed.

[21] Appl. No.: 472,886

[22] Filed: Mar. 8, 1983

Related U.S. Application Data

[63] Continuation-in-part of Ser. No. 343,709, Jan. 28, 1982, abandoned.

[51] Int. Cl.$^3$ .............................................. B01J 13/02
[52] U.S. Cl. ...................................... 264/4.6; 264/4.3; 264/4.7; 428/402.24; 427/3; 424/32
[58] Field of Search ................... 428/402.24; 264/4.33, 264/4.6, 4.7, 4.1; 424/32; 427/3

[56] References Cited

U.S. PATENT DOCUMENTS

| | | | |
|---|---|---|---|
| 3,872,023 | 3/1975 | Baum et al. | 252/316 |
| 3,886,084 | 5/1975 | Vassiliades | 252/316 |
| 3,943,063 | 3/1976 | Morishita et al. | 252/316 |
| 3,960,757 | 6/1976 | Morishita et al. | 252/316 |
| 4,166,800 | 9/1979 | Fong | 252/316 |
| 4,384,975 | 5/1983 | Fong | 252/316 |

*Primary Examiner*—Richard D. Lovering
*Assistant Examiner*—Anne Brookes
*Attorney, Agent, or Firm*—Gerald D. Sharkin; Robert S. Honor; Walter F. Jewell

[57] ABSTRACT

This invention provides for the production of microspheres in an oil-in-water emulsion process using an emulsifier, whereby solvent removal from the oil phase allows for isolation of discrete microspheres, wherein the release rate of a core material is modified by the use of an alkaline agent, e.g. sodium hydroxide, during the preparation of the microspheres.

14 Claims, No Drawings

PROCESS FOR PREPARATION OF MICROSPHERES AND MODIFICATION OF RELEASE RATE OF CORE MATERIAL

This application is a continuation-in-part of application Ser. No. 343,709 filed Jan. 28, 1982 now abandoned.

BACKGROUND OF THE INVENTION

This invention relates to microspheres. More particularly it relates to processes for the preparation of microspheres of a polymer and a core material and to products produced thereby. In one particular aspect it relates to processes for the preparation of microspheres of a polymer and a drug and to products produced thereby.

In another aspect it relates to processes for modifying the release rate of a core material by the use of an alkaline agent during the preparation of the microspheres.

Broadly, the microspheres of this invention may be described as: microcapsules of a core material, e.g., drug, and a polymer wherein the polymer coats a drug particle; or microprills which are homogeneous mixtures of a core material, e.g., drug and a polymer. The processes of this invention are directed to the modification of the release rate of a core material from microspheres by the novel use of an alkaline agent during the preparation of the microspheres.

Microencapsulation processes based on solvent removal from emulsions are known in the prior art and have been reviewed in various publications. These include: M. Morishita et al. in "Microencapsulation: Processes and Applications," edited by J. E. Vandegaer, Plenum Press, NY, 1974, pp. 115–116; A. Watanabe and T. Hayashi in "Microencapsulation," edited by M. R. Nixon, Marcel Dekker, Inc., NY, 1976, pp. 18–19; A. Kondo, "Microcapsule Processing and Technology," edited and revised by J. W. Van Valkenburg from the original 1970 Japanese edition, Marcel Dekker, Inc., NY, 1979, pp. 106–120.

The basis of the prior art processes involves dissolving or dispersing the core material in a solution of the wall-forming material dissolved in a volatile, water-immiscible organic solvent. The organic phase is emulsified with an aqueous solution containing a surface active agent to form a dispersion of oil droplets which would yield microspheres upon removal of the organic solvent by evaporation (distillation or spray-drying), solvent extraction or freeze-drying. However, the products from these processes are agglomerated microspheres and not discrete particles, suitable for example, in parenteral applications.

U.S. Pat. No. 3,660,304 discloses a method for producing oily liquid-containing microcapsules using a mixture of high and low boiling point solvents, in an oil-in-water emulsion system.

U.S. Pat. No. 3,972,023 discloses a method for producing microcapsules by solvent evaporation from an oil-in-water emulsion, followed by chemical curing to harden the resultant microcapsules. The wall-forming polymer contains crosslinkable reactive groups.

Solvent removal from an emulsion is disclosed in U.S. Pat. No. 3,523,906 and U.S. Pat. No. 3,523,907 wherein an aqueous solution as core material was encapsulated by the emulsion method using a hydrophilic colloid such as gelatin or polyvinyl alcohol as the emulsifier.

The use of the emulsion process for microencapsulation of medicaments is described in U.S. Pat. No. 3,960,757 wherein a hydrophilic colloid (e.g., gelatin, polyvinyl alcohol) and/or a surface active agent (anionic or nonionic type having an HLB of not less than 10) is used as the emulsifier.

A mixed gelatin-nonionic surface active agent system in a similar process for preparing beads of biodegradable polymer e.g., polylactic acid containing progesterone was used by S. Yolles et al. in "Controlled Release Polymeric Formulations," edited by D. R. Paul and F. W. Harris, American Chemical Society, Washington, D.C., 1976, pp. 124–125. The microspheres formed were 250–420 micron diameter with some agglomerates present.

A process using an anionic surfactant, sodium dodecyl sulfate, in the emulsion process to encapsulate pesticides with polylactic acid is described in U.S. Pat. No. 4,272,398. The product was a coarse powder of large aggregates of microspheres, most of which were 177–595 microns.

Polyvinyl alcohol was employed as the emulsifier in a solvent evaporation process for obtaining microspheres of polylactic acid by L. R. Beck et al., "A New Long-Acting Injectable Microcapsule System for the Admiministration of Progesterone," Fertility and Sterility 31:5, 545–551 (1979). The microspheres were 10–250 microns and were free of agglomerates.

Using biodegradable polymers such as polylactic acid as the wall-forming material in microspheres for injectable application eliminates the need for surgical removal of the microspheres after delivery of the drug. For controlled release of drug suitable for parenteral administration, the microspheres should be free of agglomerates and the size should be large enough to provide adequate duration of release yet small enough not to restrict passage through the standard syringe needles. Thus, the maximum size would be about 150 microns for a conventional No. 20 gauge needle.

Although one of the major objectives of microencapsulation is to control the release rate of a core material, the prior art generally does not disclose a method for modifying a release rate.

SUMMARY OF THE INVENTION

Broadly, this invention provides for the production of microspheres in an oil-in-water emulsion process using an emulsifier, whereby solvent removal from the oil phase allows for isolation of discrete microspheres, wherein the release rate of a core material is modified by the use of an alkaline agent, e.g. sodium hydroxide, during the preparation of the microspheres.

The microcapsules of this invention comprising a polymer and a core material, e.g., drug, may be prepared by dissolving the polymer in a volatile, water-immiscible organic solvent in which the drug is not soluble; adding the drug particles; mixing the organic dispersion with an aqueous solution containing an emulsifier and an alkaline agent to form a stable oil-in-water emulsion; and removing the organic solvent by evaporation to form discrete microcapsules.

The microprills of this invention comprising a homogeneous mixture of polymer and core material, e.g., drug, may be prepared by dissolving both the polymer and drug in a volatile, water-immiscible organic solvent; mixing the organic phase with an aqueous solution containing an emulsifier and an alkaline agent to form a stable oil-in-water emulsion; and removing the organic solvent by evaporation to form discrete microprills.

The essential feature of this invention is the use of an alkaline agent during the preparation of the microspheres to modify the release rate of the core material from the microspheres.

DESCRIPTION OF THE PREFERRED EMBODIMENT

The formation of microcapsules of this invention is based on solvent removal from an oil-in-water emulsion. When an emulsion containing oil droplets formed from a dispersion of solid drug particles in a polymer solution is being evaporated, the initial removal of solvent causes the polymer to precipitate in a viscous liquid state and envelope the solid drug particles while maintaining the spherical configuration. Complete removal of solvent yields hardened, hetereogeneous microcapsules of polymer and drug particles.

The formation of microprills of this invention is also based on solvent removal from an oil-in-water emulsion. When an emulsion containing oil droplets formed from a homogeneous solution of polymer and drug is being evaporated, the initial removal of solvent causes both the polymer and drug to precipitate together in a viscous, liquid state while maintaining the spherical configuration. Complete removal of solvent yields hardened, homogeneous microprills of polymer and drug.

This invention is based on the unexpected discovery that the release rate of a core material from the microspheres can be increased by the presence of alkaline agent in the aqueous phase of an oil-in-water emulsion during the solvent evaporation step. Examples of water-soluble alkaline agents which are useful according to this invention include basic inorganic salts, alkaline buffer solutions and organic amines. Especially preferred are sodium and potassium hydroxides.

The amount of alkaline agent to be used in the processes of this invention is limited by the nature of the polymer, in that, degradation of the polymer by the alkaline agent is to be avoided. In general, the amount of alkaline agent useful in the processes of this invention may be from about 0.5% to about 20% of the alkaline agent based on the weight of the polymer used. A preferred range of alkaline agent is from about 0.5% to about 10% based on the weight of the polymer used.

A significant advantage of this invention was demonstrated by microspheres of poly(L-lactic acid) and thioridazine free base prepared in the presence of sodium hydroxide and sodium oleate during the solvent evaporation step. Unexpectedly, the in vitro release rate of the microencapsulated drug was almost as fast as the non-encapsulated drug. Since parenteral administration of the non-encapsulated drug causes severe tissue irritation, these microspheres offer a means of circumventing this problem without incurring a delay in therapeutic action.

Advantages associated with the use of the alkaline agent of this invention, other than modification of the core material release rate are:
  (a) Emulsifier efficiency is increased and therefore the concentration of emulsion required for a stable emulsion can be decreased.
  (b) A higher efficiency of encapsulation is realized, due to a higher partitioning of the drug into the oil phase of the emulsion.

A critical aspect of above processes involves using an effective emulsifier. The surfactant used as the emulsifier must first stabilize the oil-in-water emulsion containing the polymer-drug-solvent system against coalescing into larger droplets and subsequent "breaking" of the emulsion.

As the solvent is being evaporated, the emulsifier must also maintain these oil droplets in their spherical configuration and stabilize them against uncontrolled agglomeration until solvent removal is completed so that the hardened microspheres can be isolated as discrete particles.

Microspheres of polymer and core material can be obtained by solvent evaporation from an oil-in-water emulsion stabilized with hydrophilic colloid, e.g. polyvinyl alcohol, or with surface active agent. Carboxylic acid salt surfactants, e.g. sodium oleate and potassium oleate, are preferred as the emulsifying agent.

Examples of carboxylic acids whose salts are useful according to this invention include straight-chain fatty acids, coconut fatty acids, N-acylated sarcosine, and the like. The salts can be the alkali metal salts of the acid such as sodium and potassium salts or amine salts of ammonia and triethanolamine. The emulsifiers can be used as the ready-made salts or generated in situ by adding carboxylic acid to the oil phase and alkaline material to the aqueous phase.

Salts of fatty acids, such as sodium oleate and potassium oleate, are especially preferred for preparing injectable microspheres of biodegradable polymers because the fatty acids, being endogenous lipids, are also biodegradable and nontoxic. Mixtures of fatty acid salts are within the scope of this invention. Also mixtures of the fatty acid salts with nonionic surface active agents or with hydrophilic colloids, e.g., gelatin, are within the scope of this invention. The concentration of the emulsifier in the present processes is not critical, provided it is above the critical micelle concentration of the emulsifier.

The fatty acid salt emulsifier of this invention used for the preparation of microspheres of biodegradable polymers, e.g., polylactic acid and drug, satisfy the three major prerequisites required for parenteral applications:
  (1) discrete microspheres, free of agglomerates,
  (2) a maximum diameter of 150 microns, and
  (3) all ingredients in the microspheres, (even residual amounts), are non-toxic and pharmaceutically acceptable.

The emulsion processes require the drug to be insoluble or only slightly soluble in water. For drugs with some solubility in water, the aqueous phase can be saturated with the drug to maintain the desired concentration in the oil phase. An alternative is to add an inorganic salt to the aqueous solution to decrease solubility of the drug in the aqueous phase by the salting-out effect, provided the amount of electrolyte used does not adversely affect the performance of the emulsifier.

Another method is to convert the drug to a less soluble form. For example, prior alkaline treatment will convert the soluble acid salt of a drug to its insoluble free base.

Natural and synthetic polymers may be used in the emulsion-based processes of this invention for the preparation of microspheres. However, the polymer must be soluble in a water-immiscible solvent. For example, the polymers include cellulosic polymers, polyvinyl acetate, polyvinyl chloride, natural and synthetic rubbers, polyacrylates, polystyrene and the like. When the microspheres of this invention are intended for injectable pharmaceutical applications, biodegradable polymers such as polylactic acid, polyglycolic acid, polyhydroxybutyric acid, polycaprolactone, polyalkylene oxalate, polyalkylene glycol esters of acids of the Krebs citric acid cycle and the like and copolymers thereof may be utilized.

Illustrative of the Krebs cycle di- and tri-carboxylic acids are citric, cis-aconitic, isocitric, α-ketoglutaric, succinic, fumaric, malic and oxaloacetic. These acids or their physiologically tolerable homologues are reacted with a biologically compatible polyol compound e.g., glycerol, or a compound based on such a polyol, e.g., an ester of glycerol, as set forth in U.S. Pat. No. 3,978,203. Among the physiologically tolerable polyols are glycerol, mannitol, sorbitol, and the like.

For the preparation of microprills, the solvent selected must dissolve both polymer and active agent. For the preparation of microcapsules, the solvent must dissolve the polymer but not the dispersed core materials, e.g., drug particles. For either microprills or microcapsules, the organic solvent used for the oil phase must be immiscible or only partly soluble in water, relatively volatile, and inert to both polymer and drug.

Examples of water-immiscible solvent for the biodegradable polylactic acid polymer and its copolymers include methylene chloride, chloroform, benzene, ethyl acetate and the like.

The solvent need not be limited to a single component system and mixed solvent systems may be used. Where there is no common solvent for both the polymer and core material a mixed system may act as a common solvent in preparing microprills. For example, it may be necessary to predissolve the drug in a small volume of a water-miscible solvent before mixing with the water-immiscible solution. A variation of this mixed solvent system for the preparation of microcapsules is where the core material particles to be encapsulated have some solubility in the solvent of choice for the polymer. Sufficient amounts of another solvent may then be added to minimize drug solubility without affecting polymer solubility.

For the preparation of heterogeneous microcapsules in which the drug is insoluble or partially soluble in the organic solvent of choice, the drug particle size should be reduced for efficient microencapsulation. This can be done by micronization of the drug substance prior to dispersing in the oil phase or by mixing the drug particles-organic dispersion with an ultrasonic homogenizer prior to the emulsification step.

Solvent removal by evaporation after the emulsification step can be controlled by temperature with or without reduced pressure. This can be conducted by distillation at ambient temperature or at lower or elevated temperatures. It may also be advantageous to employ a sequential change in temperature and pressure. Solvent removal can also be accomplished by spray-drying, solvent extraction or freeze-drying the emulsion.

The core material of the microspheres prepared by the processes of this invention may be agricultural agents such as insecticides, fungicides, herbicides, rodenticides, pesticides, fertilizers, and viruses for crop protection and the like; cosmetic agents such as deodorants, fragrances and the like; food additives such as flavors, oils, fats and the like; and pharmaceutical agents.

Pharmaceutical agents, e.g., drugs, are especially preferred core materials and the invention will be further described using drugs as the core material. These drugs may be in free base form or in the form of their nontoxic, pharmaceutically acceptable acid addition salts, although the latter may be converted to the free base form by the alkaline pH used in these emulsion processes. Representatives of such salts are hydrochloride, sulfate, phosphate, succinate, benzoate, acetate, pamoate, fumarate, mesylate and the like.

The polymer-drug compositions may also include controlled release injectable, oral and topical formulations. Other pharmaceutical applications may include taste-masking of bitter drugs, separation of incompatible drugs, and the protection of drugs from moisture, light and air.

For controlled release of drug suitable for parenteral administration, the size (diameter) of the microspheres should be large enough to not restrict passage through the standard syringe needles employed. Thus, a desirable maximum size would be about 150 microns for a No. 20 gauge needle.

The processes of this invention can produce microspheres with diameters significantly less than 150 microns. For example, oil droplets of an emulsion may be reduced in size by brief ultrasonic homogenization prior to solvent removal to yield discrete microspheres of 5–25 microns, free of agglomerization. Submicron microspheres or a latex of submicron particles may be obtained by more extensive ultrasonic homogenization. The submicron particle size makes it amenable for intravenous application. These particles may also be used for oral or parenteral administration of poorly absorbing drugs due to the increased surface area available. Latex containing submicron particles of microencapsulated active material would also be suitable for topical application, including dermatological and cosmetic agents such as lotions, deodorants and fragrances.

EXAMPLE 1

(a) A solution of 1.5 g Mellaril (thioridazine free base, Sandoz, Inc.) and 1.0 g poly(L-lactic acid) in 10 ml methylene chloride was emulsified with an aqueous solution of 0.2 g sodium oleate, 15 ml 0.1N NaOH and 85 ml distilled water. The organic solvent was removed by vacuum distillation at 30° C. for 2 hours. After cooling, the product was filtered, washed with water and dried to yield 2.32 g of discrete microprills with diameter of 10–90 microns.

(b) The above procedure was repeated without the NaOH, and using 0.4 g sodium oleate in 100 ml water as the emulsifier. The yield was 2.31 g of discrete microprills with diameter of 15–100 microns.

The release rates of the microprills of thioridazine from 1(a) and 1(b) are shown in Table I. These release rates were determined by placing a sample containing the equivalent of 5.0 mg thioridazine in 1000 ml of pH 7.2 phosphate buffer. The mixture was maintained at 37° C. with stirring. Aliquots were withdrawn at various time points and the absorbance was measured at 265 nm with an ultraviolet spectrophotometer.

TABLE I

| | % Thioridazine Released | | | | | | | |
|---|---|---|---|---|---|---|---|---|
| | 15 min | 30 min | 1 hr | 2 hr | 3 hr | 1 d | 2 d | 5 d |
| 1(a) | 44 | 53 | 55 | 58 | 61 | 76 | 77 | 85 |
| 1(b) | 24 | 32 | 31 | 34 | 36 | 48 | 52 | 66 |
| Non-encapsulated | — | 50 | — | 62 | — | 100 | — | — |

TABLE I-continued

| | % Thioridazine Released | | | | | | | |
|---|---|---|---|---|---|---|---|---|
| | 15 min | 30 min | 1 hr | 2 hr | 3 hr | 1 d | 2 d | 5 d |
| Thioridazine | | | | | | | | |

The release rate was faster for the microprills prepared with NaOH than those prepared without NaOH. The NaOH prepared microprills had a release rate similar to the non-encapsulated drug.

EXAMPLE 2

(a) A solution of 1.0 g thioridazine free base and 1.0 g poly(D,L-lactic acid) in 10 ml methylene chloride was emulsified with an aqueous solution of 0.4 g sodium oleate, 15 ml 0.1N NaOH and 85 ml distilled water. The organic solvent was removed by vacuum distillation at 40° C. for 2 hours. The product was filtered, washed with water and dried to yield 1.69 g of discrete microprills with diameter of 10–75 microns.

(b) The above procedure was repeated without the NaOH, and using 0.4 g sodium oleate in 100 ml water as the emulsifier. The yield was 1.59 g of discrete microprills with diameter of 15–85 microns.

The release rates of thioridazine from the microprills of 2(a) and 2(b) are shown in Table II.

TABLE II

| | % Thioridazine Released | | | | | | | | | |
|---|---|---|---|---|---|---|---|---|---|---|
| | 1 hr | 4 hr | 1 d | 2 d | 3 d | 7 d | 8 d | 9 d | 10 d | 28 d |
| 2(a) | 15 | 25 | 32 | 36 | 44 | 76 | 90 | 91 | 100 | — |
| 2(b) | 7 | 7 | 10 | 13 | 13 | 36 | 36 | 42 | 46 | 88 |
| Non-encapsulated Thioridazine | — | 75 | 100 | — | — | — | — | — | — | — |

The release rate was faster for the microprills prepared with NaOH. Both the NaOH prepared microprills and those prepared without NaOH had release rates which were slower than the non-encapsulated drug. Poly (D,L-lactic acid) was used in this example and the release rates of the microprills differ from the microprills in Example 1 where poly(L-lactic acid) was used.

EXAMPLE 3

(a) A solution of 1.5 g thioridazine free base and 1.0 g poly(D,L-lactic acid) in 10 ml methylene chloride was emulsified with an aqueous solution of 0.4 g polyvinyl alcohol, 15 ml 0.1N NaOH and 85 ml distilled water. The organic solvent was removed by vacuum distillation at room temperature for 5 hours. The product was filtered, washed with water and dried to yield 2.04 g of discrete microprills with diameter of 15–75 microns.

(b) The above experiment was repeated without NaOH, using 0.4 g polyvinyl alcohol in 100 ml water as the emulsifier. The yield was 1.97 g of discrete microprills with diameter of 20–85 microns.

The release rates of thioridazine from the microprills of 3(a) and 3(b) are shown in Table III.

TABLE III

| | % Thioridazine Released | | | | | | | |
|---|---|---|---|---|---|---|---|---|
| | 4 hr | 1 d | 2 d | 3 d | 4 d | 9 d | 10 d | 11 d |
| 3(a) | 18 | 38 | 69 | 76 | 81 | 92 | 100 | — |
| 3(b) | 8 | 9 | 11 | 18 | 19 | 84 | 95 | 100 |
| Non-encapsulated | 75 | 100 | — | — | — | — | — | — |

TABLE III-continued

| | % Thioridazine Released | | | | | | | |
|---|---|---|---|---|---|---|---|---|
| | 4 hr | 1 d | 2 d | 3 d | 4 d | 9 d | 10 d | 11 d |
| Thioridazine | | | | | | | | |

The release rate was faster for the microprills prepared with NaOH. Both the NaOH prepared microprills and those prepared without NaOH had release rates which were slower than the non-encapsulated drug.

EXAMPLE 4

(a) A dispersion of 1.0 g ketotifen hydrogen fumarate (Zaditen, Sandoz, Inc.) and 1.0 g poly(L-lactic acid) in 10 ml methylene chloride was mixed with 47 ml 0.1N NaOH, the stoichiometric amount required to convert ketotifen hydrogen fumarate to the ketotifen free base. The neutral mixture was then emulsified with an aqueous solution of 0.4 g sodium oleate, 15 ml 0.1N NaOH and 40 ml distilled water. The organic solvent was removed by vacuum distillation at 40° C. for 2 hours. After cooling, the product was filtered, washed with water and dried to yield 1.43 g of discrete microprills with diameter of 15–120 microns.

(b) The above procedure was repeated with the neutral mixture emulsified with 0.4 g sodium oleate in 53 ml water without NaOH. The yield was 1.45 g of discrete microprills with diameter of 15–85 microns.

The release rates were determined by placing microprills containing the equivalent of 20.0 mg ketotifen base in 1000 ml of pH 7.2 phosphate buffer. The mixture was maintained at 37° C. with stirring. Aliquots were withdrawn at various time points and the absorbance was measured at 300 nm with an ultraviolet spectrophotometer.

TABLE IV

| | % Ketotifen Base Released | | | | | |
|---|---|---|---|---|---|---|
| | 4 hr | 1 d | 2 d | 3 d | 4 d | 7 d |
| 4(a) | 3 | 3 | 34 | 72 | 86 | 90 |
| 4(b) | 3 | 3 | 4 | 29 | 76 | 80 |
| Non-encapsulated Ketotifen | 100 | — | — | — | — | — |

The release rate was faster for the microprills prepared with NaOH. Both the NaOH prepared microprills and those prepared without NaOH had release rates which were slower than the non-encapsulated drug.

EXAMPLE 5

(a) A dispersion of 1.0 g ketotifen hydrogen fumarate and 1.0 g poly(D,L-lactic acid) in 10 ml methylene chloride was mixed with 47 ml 0.1N NaOH, the stoichiometric amount required to convert the ketotifen hydrogen fumarate to ketotifen free base. The neutral mixture was then emulsified with an aqueous solution of 0.4 g sodium oleate, 15 ml 0.1N NaOH and 40 ml distilled water. The organic solvent was removed by vacuum distillation at 40° C. for 2 hours. After cooling, the product was filtered, washed with water and dried to yield 1.3 g of discrete microprills with diameter of 10–65 microns.

(b) The above experiment was repeated with the neutral mixture emulsified with 0.4 g sodium oleate in 53 ml water without NaOH. The yield was 1.28 g of discrete microprills with diameter of 15–75 microns.

The release rates of ketotifen base from the microprills of 5(a) and 5(b) are shown in Table V below.

TABLE V

| | % Ketotifen Base Released | | | | | | |
|---|---|---|---|---|---|---|---|
| | 4 hr | 1 d | 2 d | 3 d | 7 d | 10 d | 15 d |
| 5(a) | 3 | 9 | 14 | 34 | 68 | 82 | 87 |
| 5(b) | 2 | 4 | 7 | 13 | 50 | 65 | 80 |
| Non-encapsulated Ketotifen | 100 | — | — | — | — | — | — |

The release rate was faster for the microprills prepared with NaOH. Both the NaOH prepared microprills and those prepared without NaOH had release rates which were slower than the non-encapsulated drug. Poly(D,L-lactic acid) was used in this example and the release rates of the microprills differ from the microprills in Example 4 where poly(L-lactic acid) was used.

EXAMPLE 6

(a) A solution of 1.0 g temazepam (Sandoz, Inc.) and 1.0 g poly(D,L-lactic acid) in 10 ml methylene chloride was emulsified with an aqueous solution of 0.1 g sodium oleate, 2.5 ml 0.1N NaOH and 47.5 ml distilled water. The organic solvent was removed by vacuum distillation at 40° C. for 30 minutes. The product was filtered to yield 1.8 g of microprills with diameter of 20-100 microns.

(b) The above procedure was repeated with a higher level of NaOH, using an aqueous solution of 0.1 g sodium oleate, 7.5 ml 0.1N NaOH and 42.5 ml water.

(c) The procedure of (a) above was repeated without NaOH, using 0.12 g sodium oleate in 60 ml water as the emulsifier.

The release rates of temazepam from the microprills of 6(a), 6(b) and 6(c) are shown in Table VI. The release rates were determined by placing microprills containing the equivalent of 10.0 mg temazepam in 1000 ml of pH 7.4 phosphate buffer. The mixture was maintained at 37° C. with stirring. Aliquots were withdrawn at various time points and the absorbance was measured at 310 nm with an ultraviolet spectrophotometer.

TABLE VI

| | % Temezapam Released | | | | | | | |
|---|---|---|---|---|---|---|---|---|
| | 1 hr | 4 hr | 1 d | 2 d | 3 d | 4 d | 7 d | 10 d |
| 6(a) | 26 | 42 | 65 | 65 | 73 | 74 | 92 | — |
| 6(b) | 29 | 49 | 88 | 95 | 99 | — | — | — |
| 6(c) | 16 | 22 | 26 | 36 | 41 | 46 | 59 | 77 |
| Non-encapsulated Temezapam | 28 | 43 | 100 | — | — | — | — | — |

The release rate was faster for the microprills prepared with NaOH than those prepared without NaOH. The release rates were proportional to the level of NaOH used: faster at the higher level of NaOH, slower at the lower level of NaOH used.

EXAMPLE 7

A solution of 1.5 g thioridazine free base and 1.0 g poly(75:25 DL-lactic acid/glycolic acid) copolymer in 10 ml methylene chloride was emulsified with an aqueous solution of 0.2 g sodium oleate, 15 ml 0.1N NaOH and 85 ml distilled water. The organic solvent was removed by vacuum distillation at 40° C. for 2 hours. After cooling, the product was filtered, washed with water and dried to yield 1.98 g of discrete microprills with diameter of 20-100 microns.

The release rate of thioridazine is shown in Table VII.

TABLE VII

| % Thioridazine Released | | | | |
|---|---|---|---|---|
| 1 d | 2 d | 3 d | 4 d | 7 d |
| 36 | 50 | 74 | 83 | 90 |

EXAMPLE 8

A solution of 1.5 g thioridazine free base (Sandoz, Inc.) and 1.0 g poly(90:10 DL-lactic acid/epsilon-caprolactone) copolymer in 10 ml methylene chloride was emulsified with an aqueous solution of 0.2 g sodium oleate, 15 ml 0.1N NaOH and 85 ml distilled water. The organic solvent was removed by vacuum distillation at 40° C. for 2 hours. After cooling, the product was filtered, washed with water and dried to yield 2.17 g of discrete microprills with diameter of 20-150 microns.

The release rate of thioridazine is shown in Table VIII.

TABLE VIII

| % Thioridazine Released | | | | | |
|---|---|---|---|---|---|
| 1 d | 2 d | 3 d | 6 d | 7 d | 10 d |
| 49 | 56 | 60 | 76 | 88 | 100 |

EXAMPLE 9

(a) A solution of 1.0 g Parlodel ® (bromocriptine mesylate, Sandoz, Inc.) in 2 ml methanol was mixed with a solution of 1.0 g poly(D,L-lactic acid) in 10 ml methylene chloride. The organic solution was emulsified by swirling with an aqueous solution of 0.2 g sodium oleate, 55 ml distilled water and 45 ml 0.1N NaOH, which is 31.7 ml more than the stoichiometric amount required to convert the bromocriptine mesylate to bromocriptine free base. The organic solvents were removed by vacuum distillation at 40° C. for 2 hours. The product was filtered, washed with water and dried to yield 1.75 g of discrete microprills with diameter of 20-100 microns.

(b) The above procedure was repeated with the organic solution emulsified with 0.2 g sodium oleate, 85 ml distilled water and 15 ml 0.1N NaOH, which is 1.7 ml more than the stoichiometric amount required to convert the bromocriptine mesylate to bromocriptine free base. The yield was 1.71 g of discrete microprills with diameter of 25-90 microns.

The release rate of bromocriptine base from the microprills of 9(a) and 9(b) was determined by placing a sample containing the equivalent of 90 mg drug in 1000 ml of pH 3.4 citrate buffer solution. The mixture was stirred at room temperature. Aliquots were withdrawn at various time points and the absorbance was measured at 300 nm with an ultraviolet spectrophotometer. The results are shown in Table IX.

TABLE IX

| | % Bromocriptine Base Released | | | |
|---|---|---|---|---|
| | 1 hr | 4 hr | 1 d | 2 d |
| 9(a) | 82 | 92 | 96 | 100 |
| 9(b) | 6 | 13 | 13 | 17 |

The release rates were proportional to the level of NaOH used: faster at the higher level of NaOH, slower at the lower level of NaOH used.

EXAMPLE 10

A solution of 0.5 g Hydergine ® free base (dihydroergocornine, dihydroergocristine and dihydroergokryptine, Sandoz, Inc.) in 2 ml methanol was mixed with a solution of 0.5 g poly(D,L-lactic acid) in 10 ml methylene chloride. The organic solution was emulsified with an aqueous solution of 0.1 g sodium oleate, 7.5 ml 0.1N NaOH and 42.5 ml distilled water. The organic solvents were evaporated by stirring in an open beaker at room temperature for 3 hours. The product was filtered, washed with water and dried. The yield was 0.85 g of discrete microprills of 25–125 micron diameter.

What is claimed is:

1. In a process for the preparation of microspheres having a particulate core material encapsulated by a polymer coating wherein the polymer is dissolved in a volatile water-immiscible solvent in which the core material is not soluble, adding the core material particles, mixing the resulting dispersion with an aqueous emulsifier solution to form an oil-in-water emulsion, and removing the solvent to form discrete microcapsules, the improvement which comprises adding from about 0.5 to about 20 percent based on the weight of the polymer of a basic inorganic salt, an alkaline buffer solution or an organic amine as an alkaline agent to a sodium oleate, potassium oleate, or polyvinyl alcohol aqueous emulsifier solution for mixing with the dispersion, wherein the alkaline agent modifies the release rate of the core material from the microcapsules.

2. The process according to claim 1 wherein the alkaline agent is sodium hydroxide or potassium hydroxide.

3. The process according to claim 2 wherein the polymer is a biodegradable polymer.

4. The process according to claim 3 wherein the biodegradable polymer is polylactic acid, poly(lactic acid/glycolic acid) copolymer, or poly(lactic acid/epsilon-caprolactone) copolymer.

5. The process according to claim 4 where in the core material is a drug.

6. The process according to claim 5 wherein the drug is thioridiazine, ketotifen, temazepam, bromocriptine, or a mixture of dihydroergocornine, dihydroergocristine, and dihydroergokryptine, or acid addition salts thereof.

7. The process according to claim 1 wherein the amount of alkaline agent is from about 0.5 to about 10 percent.

8. In a process for the preparation of microspheres having a homogeneous mixture of polymer and core material wherein both the polymer and core material are dissolved in a volatile, water immiscible solvent, mixing the polymer-core material-solvent system with an aqueous emulsifier solution to form an oil-in-water emulsion and removing the solvent to form discrete microprills, the improvement which comprises adding from about 0.5 to about 20 percent based on the weight of the polymer of a basic inorganic salt, an alkaline buffer solution or an organic amine as in alkaline agent to a sodium oleate, potassium oleate, or polyvinyl alcohol aqueous emulsifier solution for mixing with the polymer-core material-solvent system, wherein the alkaline agent modifies the release rate of the core material from the microcapsules.

9. The process according to claim 8 wherein the alkaline agent is sodium hydroxide or potassium hydroxide.

10. The process according to claim 9 wherein the polymer is a biodegradable polymer.

11. The process according to claim 10 wherein the biodegradable polymer is polylactic acid, poly(lactic acid/glycolic acid)copolymer, or poly(lactic acid/epsilon-caprolactone) copolymer.

12. The process according to claim 11 where in the core material is a drug.

13. The process according to claim 12 wherein the drug is selected from the group consisting of thioridazine, ketotifen, temazepam, bromocriptine, or a mixture of dihydroergocornine, dihydroergocristine, and dihydroergokryptine, or acid addition salts thereof.

14. The process according to claim 8 wherein the amount of alkaline agent is from about 0.5 to about 10 percent.

* * * * *